United States Patent
Kim et al.

(10) Patent No.: US 9,178,229 B2
(45) Date of Patent: Nov. 3, 2015

(54) MEMBRANE HUMIDIFIER FOR FUEL CELL

(75) Inventors: Hyun Yoo Kim, Gyeonggi-do (KR); Hyuck Roul Kwon, Gyeonggi-do (KR)

(73) Assignees: Hyundai Motor Company, Seoul (KR); Kia Motors Corporation, Seoul (KR)

(*) Notice: Subject to any disclaimer, the term of this patent is extended or adjusted under 35 U.S.C. 154(b) by 866 days.

(21) Appl. No.: 13/107,177

(22) Filed: May 13, 2011

(65) Prior Publication Data

US 2012/0231357 A1   Sep. 13, 2012

(30) Foreign Application Priority Data

Mar. 9, 2011   (KR) .................. 10-2011-0020957

(51) Int. Cl.
| | |
|---|---|
| *B01D 63/02* | (2006.01) |
| *B01D 63/06* | (2006.01) |
| *H01M 8/04* | (2006.01) |
| *A61M 16/16* | (2006.01) |

(52) U.S. Cl.
CPC ........... *H01M 8/04149* (2013.01); *A61M 16/16* (2013.01); *A61M 2205/7536* (2013.01); *Y02E 60/50* (2013.01)

(58) Field of Classification Search
CPC ............ H01M 8/04119; H01M 8/04126; F24F 6/04; F24F 6/043; B01D 63/02; B01D 63/04; B01D 63/06; B01D 63/043; B01D 63/046; B01D 53/22; B01D 53/268
USPC ........... 429/413, 414, 439, 434, 435; 261/104
See application file for complete search history.

(56) References Cited

U.S. PATENT DOCUMENTS

| | | | | |
|---|---|---|---|---|
| 6,554,261 | B2 * | 4/2003 | Katagiri et al. | 261/154 |
| 6,659,433 | B2 * | 12/2003 | Kusano et al. | 261/102 |
| 7,858,247 | B2 * | 12/2010 | Kim | 429/413 |
| 2001/0015500 | A1 * | 8/2001 | Shimanuki et al. | 261/104 |

FOREIGN PATENT DOCUMENTS

| | | |
|---|---|---|
| JP | 2002-075421 A | 3/2002 |
| JP | 2003178781 A | 6/2003 |
| JP | 2005098695 A | 4/2005 |
| JP | 2008084646 A | 4/2008 |
| KR | 10-2005-0069270 | 7/2005 |
| KR | 10-2009-0043670 | 5/2009 |
| KR | 10-2010-0108092 | 10/2010 |
| WO | WO2011122822 | * 3/2011 |

* cited by examiner

*Primary Examiner* — Ula C Ruddock
*Assistant Examiner* — Thomas Parsons
(74) *Attorney, Agent, or Firm* — Mintz Levin Cohn Ferris Glovsky and Popeo, P.C.; Peter F. Corless (57) ABSTRACT

A membrane humidifier is provided for a fuel cell. The membrane humidifier of the present invention includes a hollow housing, a joint member, a plurality of internal partition modules, and a plurality of hollow fiber membrane bundles. The hollow housing has a humid air inlet formed at one end thereof and a humid air outlet formed at the other end thereof. The joint member is formed integrally with an inner circumferential surface of the hollow housing. The plurality of internal partition modules are coupled to the joint member and arranged adjacent to each other in the hollow housing, and have a plurality of humid air guiding apertures passing therethrough. The plurality of hollow fiber membrane bundles are disposed in the plurality of internal partition modules, respectively.

5 Claims, 9 Drawing Sheets

MEMBRANE HUMIDIFIER FOR FUEL CELL

CROSS-REFERENCE TO RELATED APPLICATION

This application claims under 35 U.S.C. §119(a) the benefit of Korean Patent Application No. 10-2011-0020957 filed Mar. 9, 2011, the entire contents of which are incorporated herein by reference.

BACKGROUND (a) Technical Field

The present invention relates to a membrane humidifier for a fuel cell. More particularly, it relates to a membrane humidifier for a fuel cell that can improve to humidification efficiency by forming a plurality of internal partition modules including a heater in the membrane humidifier and guiding humid air to the central part of a hollow fiber membrane bundle.

(b) Background Art

For the operation of a fuel cell stack, it is necessary to humidify a polymer electrolyte membrane in the fuel cell stack. Thus, a separate membrane humidifier in which exhaust gas, i.e., humid gas discharged from the fuel cell stack, and dry air, supplied from external air, exchange humidity with each other is being used.

Examples of humidifiers which are used in the present fuel cell systems include bubblers, injections, and absorbent types. Since there is a limitation in terms the size of the engine compartment in fuel cell vehicles, membrane humidifiers that have a relatively small volume and do not require a special power resources, are being utilizes in fuel cell vehicles. Particularly, membrane humidifiers using hollow fiber membranes are being suitably used because of the beneficial size and properties.

Figure 8:
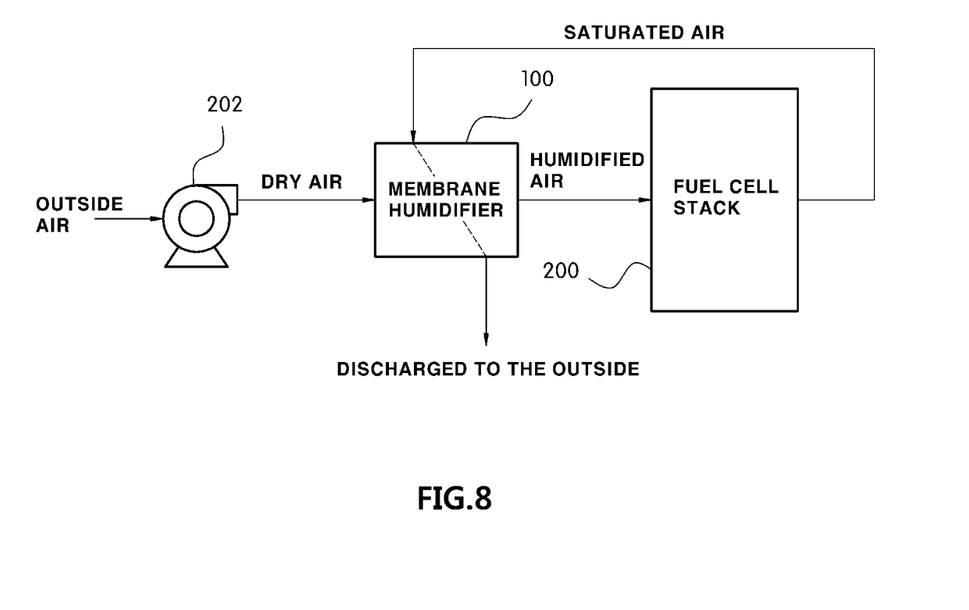
FIG. 8 is a schematic view illustrating an air supply system of a fuel cell system.

As shown in FIG. 8, in a fuel cell system, an air supply system that supplies air (oxygen) to a fuel cell stack includes a membrane humidifier. Here, a suctioning operation of an air blower 202 supplies external dry air to a membrane humidifier 100, and at the same time, exhaust gas discharged from a fuel cell stack 200 passes through the membrane humidifier 100. In this case, while humidity contained in the exhaust gas is passing through a hollow fiber membrane in the membrane humidifier 100, the dry air is humidified.

Figure 5:
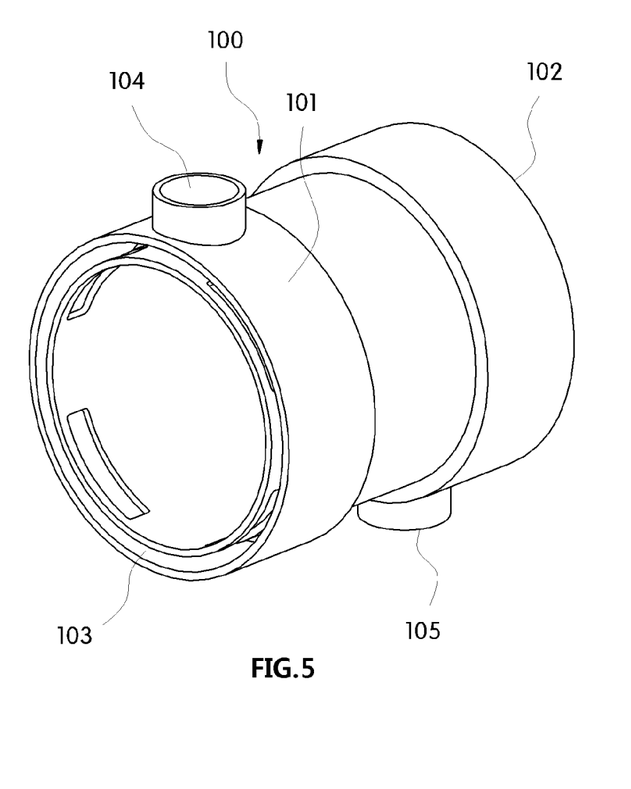
FIG. 5 is a perspective view illustrating a typical membrane humidifier for a fuel cell.
Figure 6:
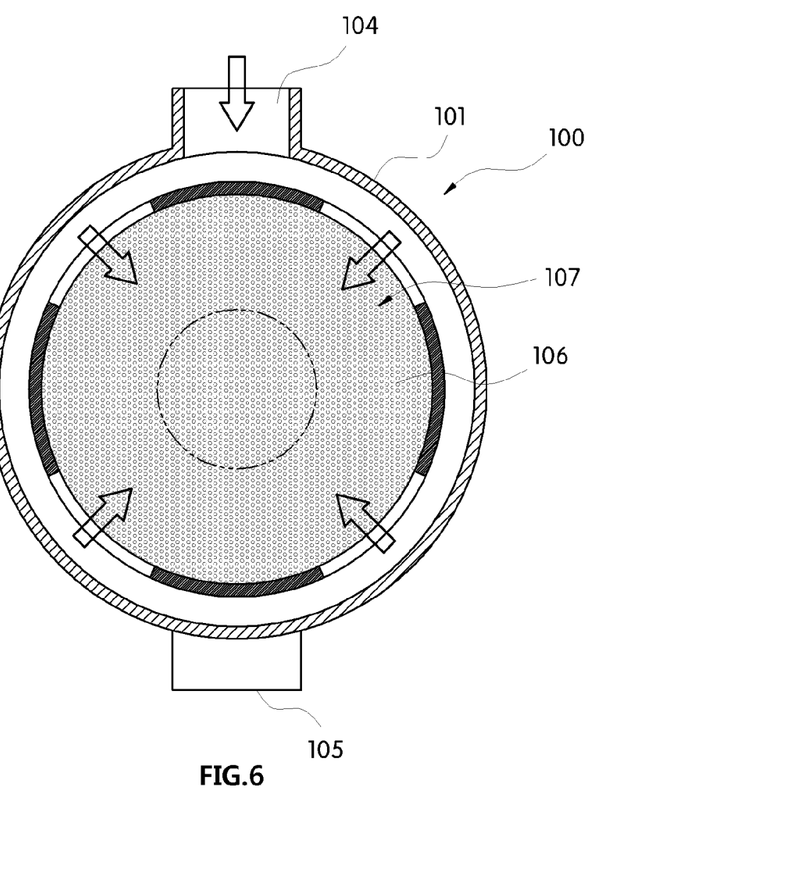
FIG. 6 is a cross-sectional view illustrating a typical membrane humidifier for a fuel cell.
Figure 7:
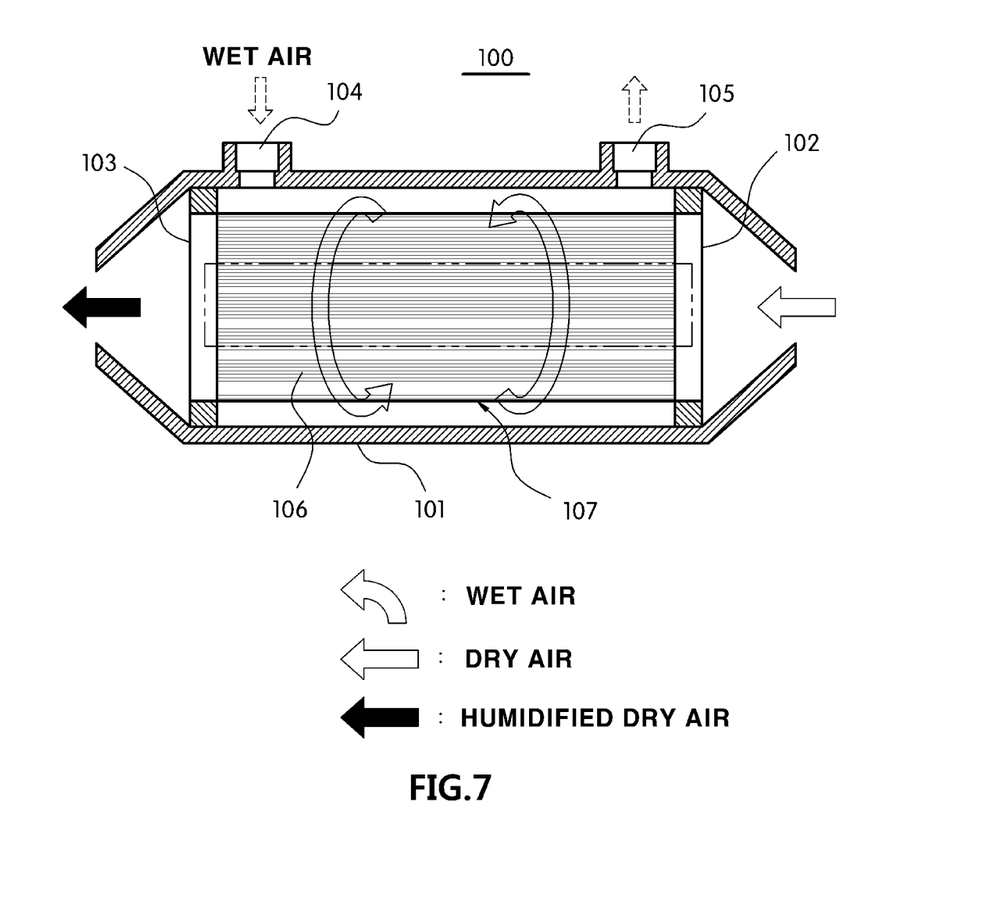
FIG. 7 is a cross-sectional view illustrating the humidification principle of a membrane humidifier for a fuel cell.

With reference to FIGS. 5 through 7, the configuration and operation of a typical membrane humidifier including a hollow fiber membrane will be described in more detail below.

Referring to FIGS. 5 through 7, a typical membrane humidifier 100 includes a housing 101. The housing 101 includes a supply port 102 for receiving dry air and a discharge port 103 for discharging humidified air. Particularly, a hollow fiber membrane bundle 107 including a plurality of hollow fiber membranes 106 is housed in the housing 101. Also, an inlet 104 for receiving humid air discharged from the fuel cell stack is formed at one side of the housing 101, and an outlet 105 for discharging humid air is formed at the opposite side of the housing 101.

Looking at the operation of a membrane humidifier using a hollow fiber membrane, when humid air, i.e., exhaust gas from a fuel cell stack is supplied from the inlet 104 of the housing 101 to the hollow fiber membrane bundle 107, humidity from the humid air is separated by a capillary action of each hollow fiber membrane 106. Here, the separated humidity is condensed while passing a capillary tube (not shown) of the hollow fiber membrane 106, and moves into the hollow fiber membrane 106. Thereafter, humidity is removed from the humid air as it moves along the outside of the hollow fiber membrane 106 to be discharged through the outlet 105 of the housing 101.

An air blower supplies external air (dry air) though the supply port 102 of the housing 101. The dry air supplied through the supply port 102 moves along the inside of the hollow fiber membrane 106. In this case, since humidity separated from the humid air has already moved to the inside of the hollow fiber membrane 106, dry air is humidified by the humidity. The humidified air is then supplied to the fuel cell stack through the discharge port 103.

However, since the hollow fiber membrane bundle 107 is a compact form of the hollow fiber membranes 106, it is difficult for the humid air introduced through the inlet 104 to penetrate into the hollow fiber membrane. Furthermore, since the diffusion speed of the humid air through the hollow fiber membrane 106 is very slow, the humid air has greater difficulty in permeating into the hollow fiber membrane 106.

Particularly, in the inside of the housing 101, the humid air passing the outside of the hollow fiber membrane bundle 107 may not permeate into the central part of the hollow fiber membrane bundle 107 that is represented as dotted lines of FIGS. 6 and 7. As shown in arrows of FIGS. 6 and 7, the humid air mostly flows along the edge of the hollow fiber membrane bundle 107. As a result, since the diffusion speed of the humid air to the central part of the hollow fiber membrane bundle 107 is very slow, the humidification efficiency with respect to dry is typically reduced. Also, since most of dry air introduced through the supply port 102 of the housing 101 flows into the central part (part represented as dotted lines of FIGS. 6 and 7) of the hollow fiber membrane bundle 107, the overall efficiency of a humidifier is even further reduced. Thus, the hollow fiber membrane 106 located at the central part of the hollow fiber membrane bundle 107 is not supplied with enough humidity, the overall efficiency of the humidifier is reduced.

Figure 9:
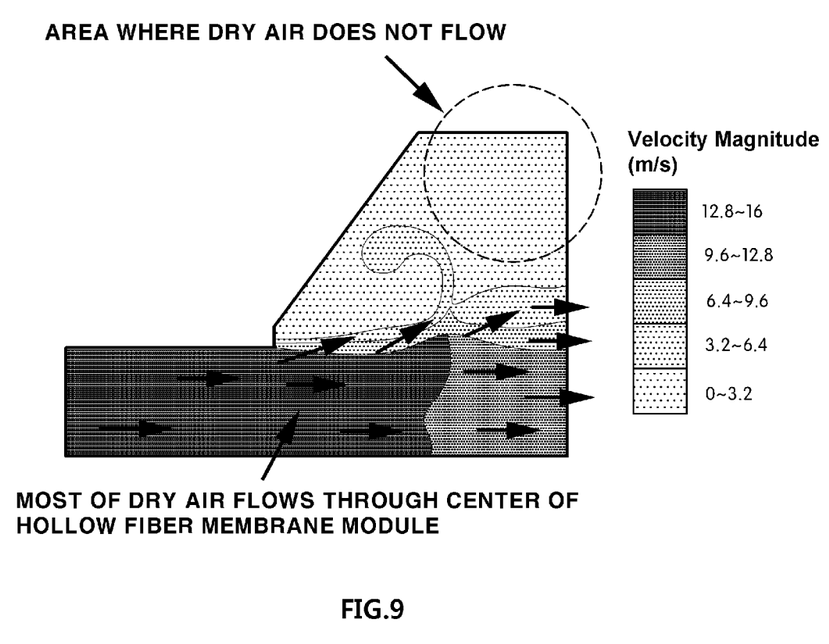
FIG. 9 is a simulation test result graph illustrating limitations occurring in a typical membrane humidifier for a fuel cell.

This limitation can be verified in a simulation test result of FIG. 9.

That is, as shown in FIG. 9, it can be verified that most of dry air flows into only the central part of the hollow fiber membrane bundle 107.

In other words, since dry air introduced through the supply port 102 of the housing 101 mostly flows along the central part (part represented as dotted line of FIGS. 6 and 7) of the hollow fiber membrane bundle 107, and humid air introduced through the inlet 104 flows along the edge part of the hollow fiber membrane bundle 107, the humidification efficiency of the membrane humidifier is reduced. This limitation has a greater influence on the humidification efficiency of the membrane humidifier as the flow rate of the dry air increases, that is, a high power is generated from the fuel cell stack.

As describe above, the humid air supplied to the membrane humidifier is air that is discharged after a reaction in the fuel cell. Generated water as well as vapor is also supplied to the membrane humidifier together with the humid air. In cold weather, water introduced into the membrane is frozen, and thus the hollow fiber membrane fails to perform its normal function due to the freezing of water. Accordingly, the frozen water has to be melted for the operation of the membrane humidifier in cold weather. If the surface of the hollow fiber membrane is damaged by repetitive freezing and melting of the surface, the damaged hollow fiber membrane has a fatal effect on the performance of the fuel cell stack. This may incur a need of full replacement of the membrane humidifier.

The hollow fiber membrane formed of polymeric material accounts for the greatest portion of the manufacturing cost of the membrane humidifier. Since a larger amount of hollow fiber membrane bundle than is needed is used to maintain excellent humidification performance, the size of the membrane humidifier may also be relatively large compared to its actual performance.

The above information disclosed in this Background section is only for enhancement of understanding of the background of the invention and therefore it may contain information that does not form the prior art that is already known in this country to a person of ordinary skill in the art.

SUMMARY OF THE DISCLOSURE

The present invention provides a membrane humidifier for a fuel cell, which can improve the humidification efficiency with respect to dry air that mostly flows along the central portion of a hollow fiber membrane bundle, by installing detachable internal partition modules of a cartridge type in a housing and allowing humid air to evenly permeate into the central part of the hollow fiber membrane bundle through an inlet of the humid air of each internal partition module.

The present invention also provides a membrane humidifier for a fuel cell, which can prevent damage of a hollow fiber membrane in advance, by installing a heating means in an internal partition module of a cartridge type to prevent freezing of water included in humid air on the surface of the hollow fiber membrane in cold weather.

In one aspect, the present invention provides a membrane humidifier for a fuel cell, including: a hollow housing having a humid air inlet formed at one end thereof and a humid air outlet formed at the other end thereof; a joint member formed integrally with an inner circumferential surface of the hollow housing; a plurality of internal partition modules coupled to the joint member, arranged adjacent to each other in the hollow housing, and having a plurality of humid air guiding apertures passing therethrough; and a plurality of hollow fiber membrane bundles disposed in the plurality of internal partition modules, respectively.

In an illustrative embodiment, the internal partition module may also include a heating coil disposed in a sidewall thereof except the humid air guiding aperture.

In another embodiment, the joint member may further include a cross-shaped support member formed integrally with the inner circumferential surface of the hollow housing, and a joint groove formed in the front side of the cross-shaped support member such that a rear end of the internal partition module is coupled thereto.

In yet another embodiment, the internal partition module may have a fan-shaped cross-section and be opened in both forward and backward directions to allow the hollow fiber membrane bundle to pass through, and have the humid air guiding apertures penetrating through sidewalls thereof.

Other aspects and embodiments of the invention are discussed infra.

BRIEF DESCRIPTION OF THE DRAWINGS

The above and other features of the present invention will now be described in detail with reference to certain exemplary embodiments thereof illustrated in the to accompanying drawings which are given hereinbelow by way of illustration only, and thus are not limitative of the present invention, and wherein.

Reference numerals set forth in the Drawings includes reference to the following elements as further discussed below:

100: membrane humidifier
101: housing
102: supply port
103: discharge port
104: inlet
105: outlet
106: hollow fiber membrane
107: hollow fiber membrane bundle
110: internal partition module 1
112: humid air guiding aperture
114: heating coil
120: joint member
122: support member
124: joint groove
200: fuel cell stack
202: air blower It should be understood that the appended drawings are not necessarily to scale, presenting a somewhat simplified representation of various features illustrative of the basic principles of the invention. The specific design features of the present invention as to disclosed herein, including, for example, specific dimensions, orientations, locations, and shapes will be determined in part by the particular intended application and use environment.

In the figures, reference numbers refer to the same or equivalent parts of the present invention throughout the several figures of the drawing.

DETAILED DESCRIPTION

Hereinafter reference will now be made in detail to various embodiments of the present invention, examples of which are illustrated in the accompanying drawings and described below. While the invention will be described in conjunction with exemplary embodiments, it will be understood that present description is not intended to limit the invention to those exemplary embodiments. On the contrary, the invention is intended to cover not only the exemplary embodiments, but also various alternatives, modifications, equivalents and other embodiments, which may be included within the spirit and scope of the invention as defined by the appended claims.

It is understood that the term "vehicle" or "vehicular" or other similar term as used herein is inclusive of motor vehicles in general such as passenger automobiles including sports utility vehicles (SUV), buses, trucks, various commercial vehicles, watercraft including a variety of boats and ships, aircraft, and the like, and includes hybrid vehicles, electric vehicles, plug-in hybrid electric vehicles, hydrogen-powered vehicles and other alternative fuel vehicles (e.g., fuels derived from resources other than petroleum). As referred to herein, a hybrid vehicle is a vehicle that has two or more sources of power, for example both gasoline-powered and electric-powered vehicles.

Hereinafter, exemplary embodiments of the present invention will be described in detail with reference to the accompanying drawings.

As described above with reference to FIGS. 5 through 7, dry air (external air) supplied by an air blower through a supply port 102 of a housing 101 of a humidifier may mostly flows along the central part of a hollow fiber membrane module 107, that is, the inside of hollow fiber membranes that are arranged at the central part of hollow fiber membrane bundles. Humid air discharged from a fuel cell stack after a reaction may be introduced through an inlet 104 of the housing 101 to mostly flow along the edge portion of the hollow fiber membrane module 107, that is, the outside of hollow fiber membranes that are arranged at the outer circumferential portion of the hollow fiber membrane module 107. Accordingly, since the chance of contact between the dry air and the humid air rarely occurs, the humidification efficiency may be reduced.

Thus, the present invention focuses on increasing the humidification efficiency by supplying humid air to the central part of a hollow fiber membrane bundle in which dry air mostly flows and increasing the chance of contact between the dry air and the humid air.

Figure 1:
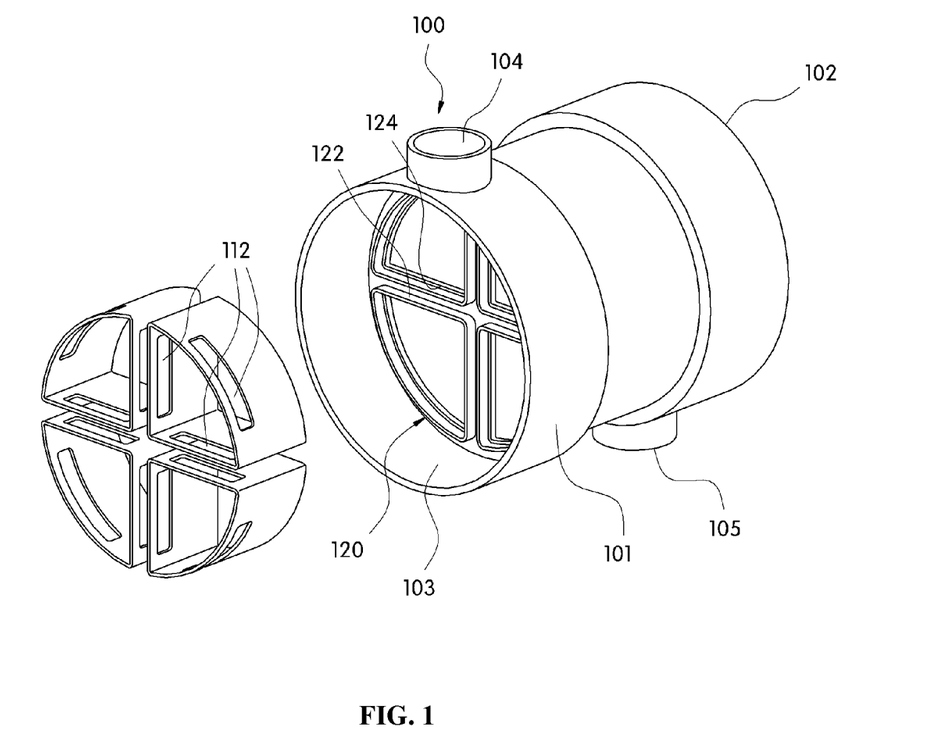
FIG. 1 is a perspective view illustrating a membrane humidifier for a fuel cell according to an exemplary embodiment of the present invention.
Figure 2:
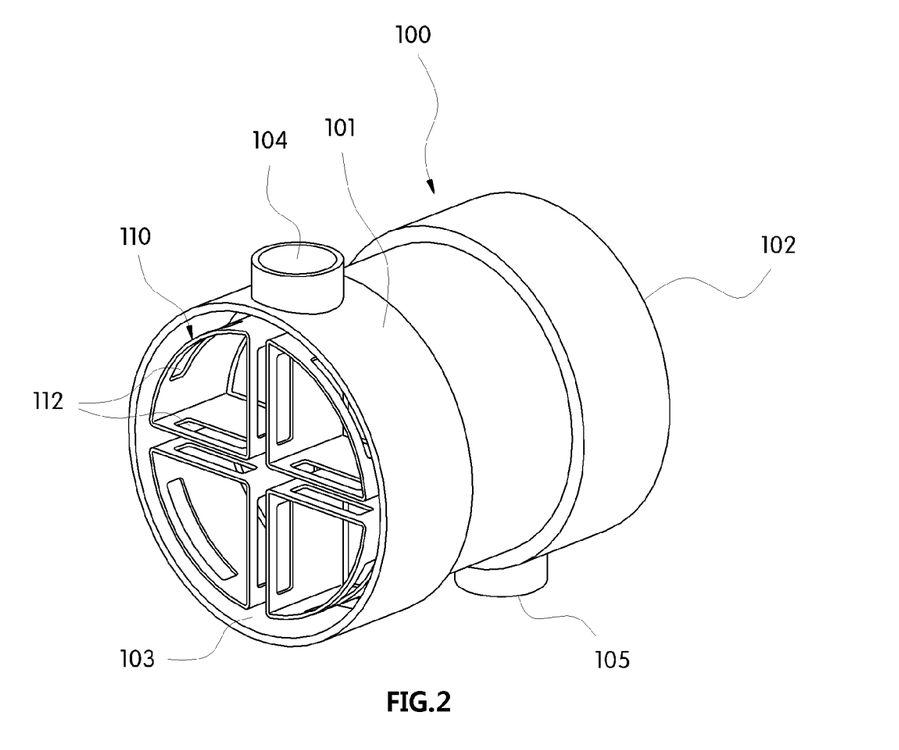
FIG. 2 is a perspective view illustrating a membrane humidifier for a fuel cell according to an exemplary embodiment of the present invention.
Figure 3:
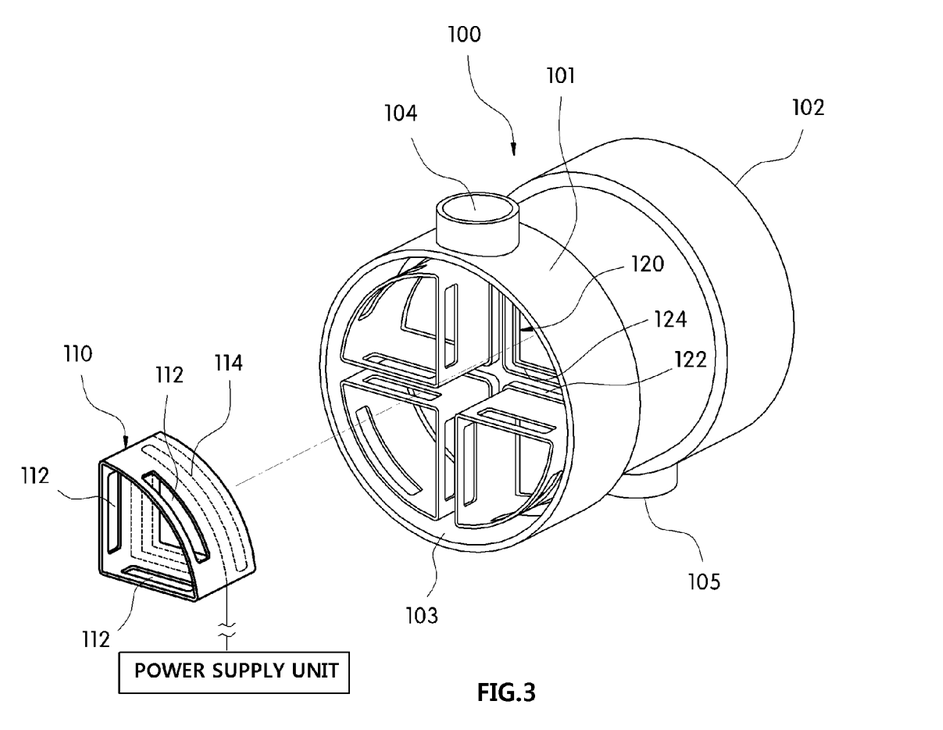
FIG. 3 is a perspective view illustrating an exemplary heating means installed in an internal partition module of a membrane humidifier for a fuel cell according to an exemplary embodiment of the present invention.

For this, as shown in FIGS. 1 through 3, a plurality of internal partition modules 110 may be detachably installed in a housing 101 of a humidifier. Hollow fiber membrane bundles may be evenly disposed in each of the internal partition modules 110 to allow humid air discharged from a fuel cell stack after a reaction to evenly permeate into the hollow fiber membranes in the internal partition module.

The housing 101 may be a hollow structure, in which an opening at one side thereof may be a supply port 102 for supplying dry air from an air blower, and an opening at the other side thereof may be a discharge port 103 for discharging humidified air to the fuel cell stack. Also, an inlet 104 for receiving humid air discharged from the fuel cell stack after a reaction may be formed at an equal interval along the circumferential direction of the discharge port 103, and an outlet 105 for discharging residual humid air may be formed in the circumferential portion of the supply port 102.

Here, the plurality of internal partition modules 110 having humid air guiding apertures 112 penetrating therethrough may be detachably installed at one side of the inside of the housing 101 in which the inlet 104 for the humid air is formed.

As an exemplary embodiment of the present invention, the internal partition module 110 may have a fan shaped cross-section, more preferably, a cross-section of a quarter of a circle. The internal partition module 110 may be opened in both forward and backward directions to allow the hollow fiber membrane bundle 106 to pass through, and the humid air guiding apertures 112 may be formed in each sidewall of the circumference of the internal partition module 110.

A joint member 120 may be integrally formed on the inner circumferential surface of the housing 101 such that the internal partition module 110 is detachably coupled to the inner circumferential surface of the housing 101. The joint member 120 may form a cross-shaped support member 122 having a joint groove 124 formed in the front side thereof. More specifically, the cross-shaped support member 122 may be formed integrally with the inner circumferential surface, and the joint groove 124 may be exposed such that the rear end of the internal partition module 110 may be coupled to the front side of the cross-shaped support member 122.

Accordingly, the internal partition module 110 may be pushed into the inner diameter of the housing 101, and at the same time, the rear end of the internal partition module 110 may be inserted into and coupled to the joint groove 124 of the cross-shaped support member 122 formed integrally with the inner circumferential surface of the housing 101.

As shown in FIGS. 1 through 4, each of the internal partition modules 110 that have a cross-section of a quarter of a circle may mutually form a cross-shaped flow path while being arranged adjacent to each other. Also, the outer sidewall of the respective internal partition modules 110 and the inner circumferential surface of the housing 101 may form an outer flow path of humid air, and may be spaced a predetermined distance from each other.

Additionally, the hollow fiber membrane bundles 107 may be disposed in the respective internal partition module 110. In this case, since the whole internal space of the respective internal partition module 110 is smaller than the internal space of a typical housing, the number of hollow fiber membrane bundles that may be arranged in the respective partition module 110 may be smaller than that of hollow fiber membrane bundles that may be densely arranged in the typical housing.

In other words, unlike a typical membrane humidifier in which a large amount of hollow fiber membrane bundles are arranged in a housing thereof, hollow fiber membrane bundles may be dispersedly arranged in each internal partition module, thereby reducing the number of expensive hollow fiber membrane bundles and promoting cost reduction Additionally, a heating coil 114 that is heated by a power supply unit may be disposed in other sidewalls of the internal partition module 110 in which the humid air guiding aperture 112 is not formed.

Hereinafter, the humidification operation of a membrane humidifier according to an embodiment of the present invention will be described in detail.

When dry air (external air) is supplied through the supply port 102 of the housing by an air blower, the dry air supplied through the supply port 102 may move through the hollow fiber membrane 106. In this case, exhaust air discharged from the fuel cell stack after a reaction, that is, humid air, may flow from the inlet 104 to the hollow fiber membrane bundles 107 of the respective internal partition module 110.

Figure 4:
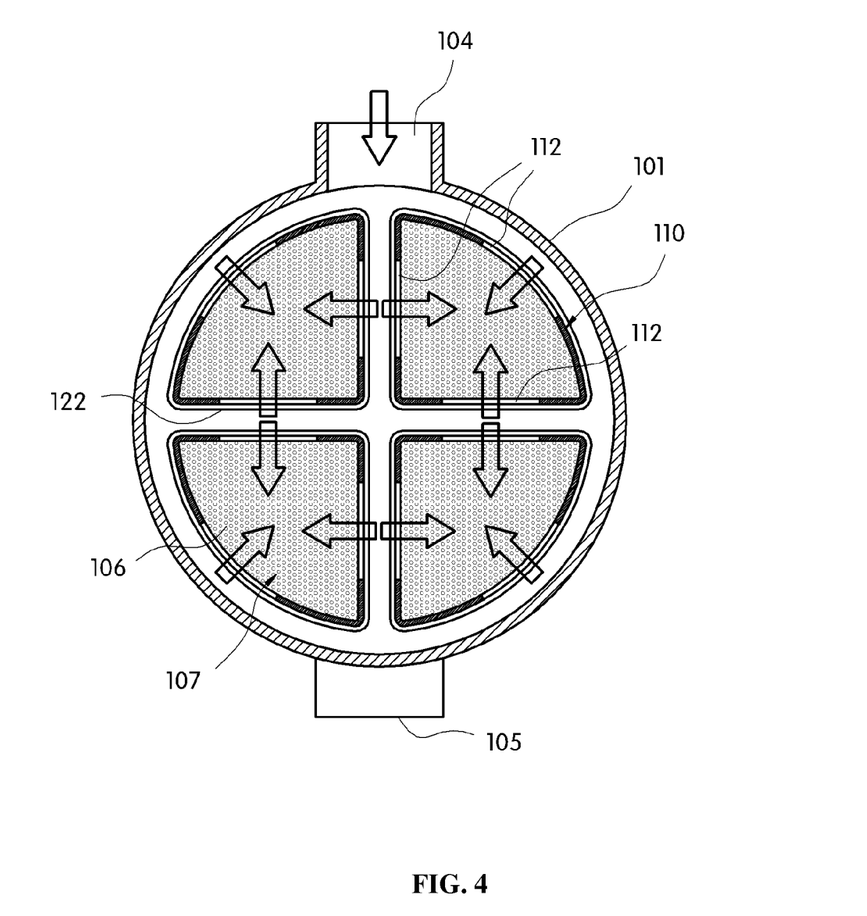
FIG. 4 is a cross-sectional view illustrating a membrane humidifier for a fuel cell according to an exemplary embodiment of the present invention.

More specifically, as shown in FIG. 4, humid air introduced through the inlet 104 of the housing may move along the cross-shaped flow path between the internal partition modules 110 and the outer flow path between the outer sidewalls of the respective internal partition modules 110 and the inner circumferential surface of the housing 101. Then, the humid air may pass the humid air guiding aperture 112 of the respective internal partition module 110, and at the same time, flow into the hollow fiber membrane to bundles 107 in the respective internal partition module 110.

Accordingly, the capillary action of the hollow fiber membranes 107 constituting the hollow fiber membrane bundles 107 in the respective internal partition module 110 may draw the humidity from the humid air. The separated humidity may be condensed while passing a capillary tube (not shown) of the hollow fiber membrane 106 and move into the respective hollow fiber membranes 106.

Thus, since the humid air is introduced through the inlet 104 of the housing 101 and evenly permeates into the hollow fiber membrane bundles 107 that are dispersedly arranged in the respective internal partition module 110, dry air flowing in the whole of the hollow fiber membrane bundle may be evenly humidified, thereby improving the humidification efficiency with respect to the dry air. The dry air may be easily humidified by the humidity that has moved to the inside of the hollow fiber membrane 106 due to the capillary action of the present invention, and then may be discharged to the fuel cell stack through the discharge port 103.

Furthermore, since power is applied to the heating coil 114 installed in the internal partition module 110 to prevent water included in humid air from being frozen on the surface of the hollow fiber membrane 106 in cold weather, it is possible to prevent the hollow fiber membrane from being damaged by freezing of water.

Advantageously, the humidification efficiency can be improved with respect to dry air that mainly flows in the central part of a hollow fiber membrane bundle, by installing detachable internal partition modules of a cartridge type in a housing of a membrane humidifier and allowing humid air discharged from a reaction in a fuel cell stack to evenly permeate into the central part of the hollow fiber membrane bundle through an inlet of the humid air of each internal partition module.

Also, unlike a conventional membrane humidifier in which a large amount of hollow fiber membrane bundles are arranged in a housing thereof, the hollow fiber membrane bundles in the present invention are dispersedly arranged in each internal partition module, thereby reducing the number of expensive hollow fiber membrane bundles and promoting cost reduction.

More particularly, a separate heating means is further installed in the internal partition module according to an embodiment of the present invention to prevent freezing of water included in humid air on the surface of the hollow fiber membrane in cold weather and prevent damage of the hollow fiber membrane due to the freezing water in advance.

The invention has been described in detail with reference to embodiments thereof. However, it will be appreciated by those skilled in the art that changes may be made in these embodiments without departing from the principles and spirit of the invention, the scope of which is defined in the appended claims and their equivalents.

What is claimed is:

1. A membrane humidifier for a fuel cell, comprising:
   a hollow housing having a humid air inlet formed at one end thereof and a humid air outlet formed at the other end thereof;
   a joint member formed integrally with an inner circumferential surface of the hollow housing;
   a plurality of internal partition modules coupled to the joint member, arranged adjacent to each other in the hollow housing, and having a plurality of humid air guiding apertures passing therethrough; and
   a plurality of hollow fiber membrane bundles disposed in the plurality of internal partition modules, respectively,
   wherein an internal flow path is formed between the internal partition modules and an outer flow path is formed between the outer sidewalls of the respective internal partition modules and the inner circumferential surface of the housing, and
   wherein the respective hollow fiber membrane bundles are connected to the internal flow path and the outer flow path through the plurality of humid air guiding apertures,
   wherein the internal partition module has a fan-shaped cross-section and is opened in both forward and backward directions to allow the hollow fiber membrane bundle to pass through, and has the humid air guiding apertures penetrating through sidewalls thereof.

2. The membrane humidifier of claim 1, wherein the internal partition module further comprise a heating coil disposed in a sidewall thereof.

3. The membrane humidifier of claim 1, wherein the joint member further comprise:
   a cross-shaped support member formed integrally with the inner circumferential surface of the hollow housing; and
   a joint groove formed in a front side of the cross-shaped support member such that a rear end of the internal partition module is coupled thereto.

4. The membrane humidifier of claim 3, wherein the internal partition module further comprise a heating coil disposed in a sidewall thereof.

5. The membrane humidifier of claim 1, wherein the internal partition module further comprise a heating coil disposed in a sidewall thereof except the humid air guiding aperture.

* * * * *